(12) United States Patent
Olson

(10) Patent No.: US 6,662,050 B2
(45) Date of Patent: Dec. 9, 2003

(54) NOTIFICATION OF PROGRAMMED STATE OF MEDICAL DEVICE

(75) Inventor: Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

(21) Appl. No.: 09/921,455

(22) Filed: Aug. 3, 2001

(65) Prior Publication Data
US 2003/0028223 A1 Feb. 6, 2003

(51) Int. Cl.⁷ .............................. A61N 1/362; A61N 1/37
(52) U.S. Cl. ......................... 607/27; 607/31; 607/30
(58) Field of Search .................... 607/4, 5, 9, 16, 607/27, 30–32, 59, 60

(56) References Cited

U.S. PATENT DOCUMENTS

| | | | |
|---|---|---|---|
| 4,582,063 A | 4/1986 | Mickiewicz et al. | 128/421 |
| 4,731,051 A | 3/1988 | Fischell | 604/67 |
| 5,350,407 A * | 9/1994 | McClure et al. | 607/16 |
| 6,068,651 A * | 5/2000 | Brandell | 607/5 |

FOREIGN PATENT DOCUMENTS

| | | | | |
|---|---|---|---|---|
| EP | 0 555 590 A2 | | 8/1993 | A61N/1/39 |
| WO | WO 99/55418 | * | 11/1999 | A61N/1/372 |
| WO | WO 01/43823 A1 | | 6/2001 | A61N/1/372 |
| WO | WO 01/52931 A1 | | 7/2001 | A61N/1/05 |

* cited by examiner

Primary Examiner—Carl Layno
(74) Attorney, Agent, or Firm—Girma Wolde-Michael; Daniel G. Chapik

(57) ABSTRACT

An implantable medical device, such as an implantable cardioverter/defibrillator (ICD) issues a notification when it has been left in a programmed state for some time, possibly inadvertently. The patient or another person may then initiate a course of corrective action, such as programming the device to an appropriate state.

33 Claims, 4 Drawing Sheets

NOTIFICATION OF PROGRAMMED STATE OF MEDICAL DEVICE

FIELD

The invention relates to implantable medical devices. More particularly, the invention relates to programmable functions in such devices.

BACKGROUND

Implantable medical devices (IMDs), such as implantable cardioverter/defibrillators (ICDs) and pacemakers (PMs), can detect and administer therapy for a variety of conditions. These conditions include ventricular fibrillation (VF), atrial fibrillation (AF), tachycardia, and bradycardia. As a particular example, an ICD receives electrical signals from the heart and processes these signals to monitor cardiac rhythms. The ICD typically includes leads that extend into the heart and support two or more defibrillation electrodes. When the ICD detects an abnormal cardiac rhythm, such as ventricular fibrillation, the ICD may deliver an electrical shock to the heart via a defibrillation electrode to restore the normal cardiac rhythm.

Under certain circumstances, it may be desirable to disable the operation of one or more functions of an IMD. For example, some operating conditions may make an ICD prone to false detection of ventricular fibrillations or other abnormal rhythms, i.e., detection of a VF when none is actually present. These operating conditions include electrocautery, diathermy, and other surgery-related procedures that involve the application of electromagnetic energy. Such procedures may generate electrical noise that interferes with accurate detection and analysis of cardiac signals.

Electrical interference resulting from such procedures may have many adverse effects. For example, the ICD may prematurely begin a blanking interval and ignore legitimate cardiac signals. As a result, the ICD may detect an arrhythmia that is not actually present and, in response to the perceived arrhythmia, deliver a defibrillation shock. This shock may provide inappropriate therapy to the patient and subject a health care provider to dangerous electric shocks.

Accordingly, surgical procedures that employ the application of electromagnetic energy may warrant temporarily disabling detection of and therapy for VF and other abnormal cardiac rhythms. Other circumstances may also warrant disabling VF detection and therapy, such as ICD oversensing troubleshooting. In addition, a do-not-resuscitate order issued by a physician may warrant permanently disabling VF detection and therapy, as well as other functions of the ICD.

One way to disable defibrillation is to temporarily deactivate the arrhythmia detection function of the ICD. Some ICDs include a reed switch, Hall switch, or other magnetically operated switch coupled to the circuitry that controls defibrillation. Placing a magnet in transcutaneous proximity to the ICD activates the switch and temporarily deactivates the arrhythmia detection function of the ICD, thereby preventing the application of defibrillation pulses.

When the magnet is moved away from the ICD, the arrhythmia detection function is re-enabled. Although using a magnet to suspend a function of an implantable device is relatively simple, this approach can fail if the magnet is improperly placed or if the magnet shifts from its proper location. In addition, it is difficult to use a magnet to disable detection and therapy functions permanently in appropriate situations, such as compliance with a do-not-resuscitate order.

Defibrillation can also be disabled by a programmer external to the ICD. To disable defibrillation, the programmer transmits a control signal to the ICD, which responds by disabling detection, therapy, or both. As a result, the ICD may stop detecting VF or other arrhythmias, or may continue detecting VF but stop administering electric shocks. In any case, once disabled, defibrillation remains inactive until reactivated by another control signal.

One problem that has been observed in connection with the use of a programmer is that health care providers sometimes inadvertently fail to reactivate defibrillation. Leaving VF detection or therapy in the disabled state places the patient at risk because no life saving therapy is administered during subsequent VF episodes. In some cases, ICDs could be inadvertently left in the disabled state for days or even months, with potentially fatal consequences.

SUMMARY

The invention is generally directed to techniques for issuing a notification when an ICD or other medical device has been left in a programmed state for some time, possibly inadvertently. For example, the medical device may issue the notification if ventricular fibrillation (VF) detection or therapy has been left in a programmed disabled state for an extended period of time. In some embodiments, the notification is issued to the patient, who may then take corrective action, such as visiting a health care provider. Alternatively, the health care provider may receive the notification and contact the patient.

One particular embodiment of the invention is directed to a method for indicating a programmed state of an implantable medical device. The programmed state is detected. At a subsequent time after detecting the programmed state, it is determined whether the implantable medical device is in the same programmed state. If so, a notification is issued. This method may be implemented using a processor-readable medium, such as a read-only memory (ROM).

The invention may also be embodied in an implantable medical device that includes a control module programmable to a programmed state. A monitoring module is capable of detecting the programmed state. An alert module issues a notification when the control module remains in the programmed state at a subsequent time after the monitoring module detects the programmed state.

The invention is capable of providing one or more advantages. By alerting a patient when the implantable medical device has been left in a potentially harmful programmed state for an extended duration, the invention may mitigate the risk of harm to the patient due to human error. For example, if ventricular fibrillation (VF) detection or therapy is programmed to a disabled state and inadvertently left in that state, i.e., is not enabled again in a timely manner, issuing an alert to the patient may prompt the patient to make an office visit to have VF detection and therapy reactivated. In addition, in some embodiments, life-critical features, such as VF detection and therapy, may be automatically reactivated without human intervention.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

In this detailed description, reference is made to the accompanying drawings, which form a part hereof, and in which are shown by way of illustration specific embodiments in which the invention may be practiced. It is to be understood that other embodiments may be utilized and structural or logical changes may be made without departing from the scope of the invention. The following detailed description, therefore, is not to be taken in a limiting sense, and the scope of the invention is defined by the appended claims.

The invention is generally directed to techniques for issuing a notification when an implantable cardioverter/defibrillator (ICD) or other medical device has been left in a programmed state for some time, possibly inadvertently. For example, the medical device may issue the notification if ventricular fibrillation (VF) detection or therapy has been left in a programmed disabled state for an extended period of time.

In some embodiments, the notification is issued to the patient, who may then take corrective action, such as visiting a health care provider to have the device programmed to the correct state. Notification can take a variety of forms, including, but not limited to, an audible warning, a vibration, and a mild electrical stimulus. Alternatively, the health care provider may receive the notification. For example, the ICD may transmit a radio signal to which an intermediary responds by contacting a physician by telephone, paging, or electronic mail.

Figure 1:
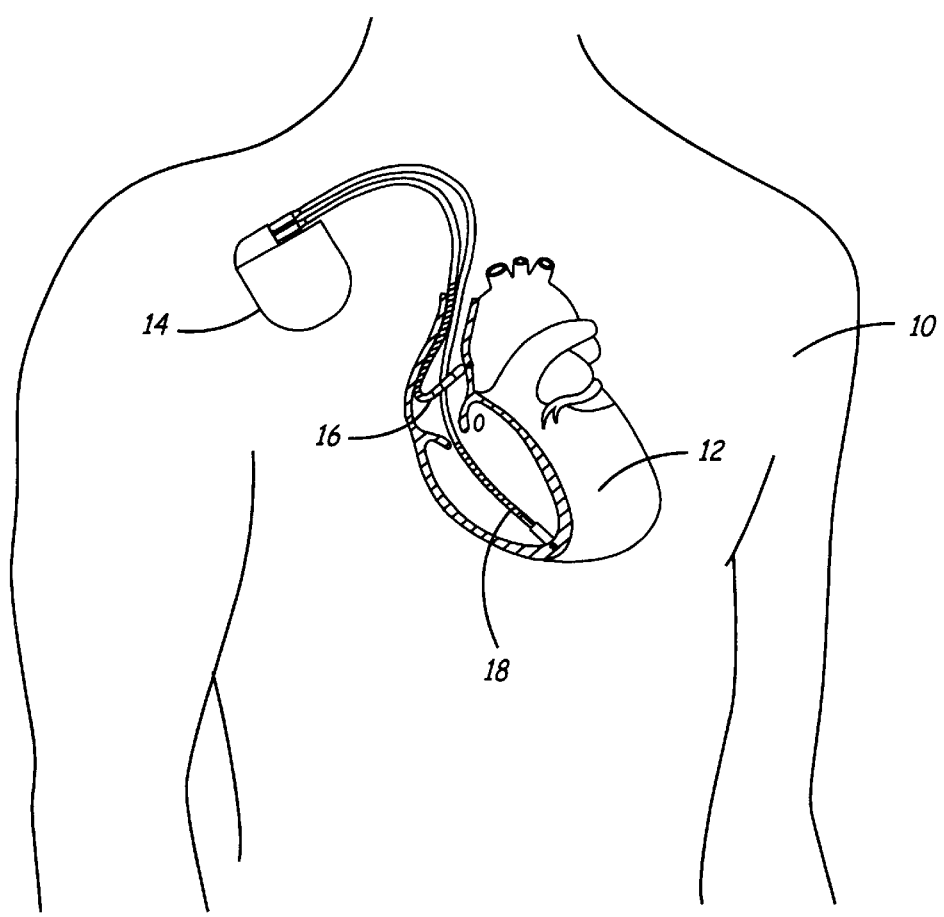
FIG. 1 is a diagram illustrating an implantable medical device, including a defibrillator, in the body of a patient.

FIG. 1 shows a typical placement of an example implanted medical device in a patient 10. FIG. 1 depicts an ICD 14, but the invention may be practiced in connection with other types of implantable medical devices, such as implantable pacemakers (PMs). Leads 16 and 18 extend from ICD 14 into a heart 12 of patient 10. Leads 16 and 18 may enter the vascular system at any of a number of entry sites, such as the cephalic vein. As depicted in FIG. 1, lead 16 is disposed in the right atrium and lead 18 is disposed in the right ventricle. Lead 16 or lead 18, or both, may be equipped with defibrillation electrodes, under the control of ICD 14. Leads 16 and 18 may also include sensing electrodes that sense the electrical activity of heart 12.

ICD 14 is implanted near the right shoulder of patient 10. This implantation site is one of many implantation sites, and the invention is not limited to use at this site. Moreover, the implantation may be implanted below the skin, or below one or more muscles, such as the pectoral muscle. The invention may be practiced with implanted medical devices at a variety of subcutaneous locations.

An external programmer (not shown) can program ICD 14 by transmitting radio frequency control signals to a receiver associated with ICD 14. In particular, the programmer can enable or disable certain functions of ICD 14 when deemed medically advisable. For example, before ICD 14 is subjected to electromagnetic noise, e.g., in connection with electrosurgery, the health care personnel may use the programmer to disable detection of and therapy for ventricular fibrillation (VF) and other arrhythmias to prevent inappropriate delivery of electrical shocks. VF detection or therapy, or both, may also be disabled for diagnostic purposes. As discussed above, users may inadvertently leave the detection or therapy function in the disabled state that can produce adverse effects, such as death, in patient 10.

As another example, the programmer can enable an arrhythmia induction mode in ICD 14, in which ICD 14 induces an arrhythmia for diagnostic purposes. For obvious reasons, this mode is generally activated only under direct medical supervision. Inadvertently leaving ICD 14 in this mode can also result in harm to patient 10.

To reduce the likelihood of inadvertently leaving ICD 14 in a programmed state, either enabled or disabled, ICD 14 incorporates a notification system that alerts the patient or another person when ICD 14 has been left in the programmed state for some duration. This duration may be defined as a set amount of time after ICD 14 was first placed in the programmed state. Alternatively, the duration may be defined as a set time of day following placing ICD 14 in the programmed state.

Figure 2:
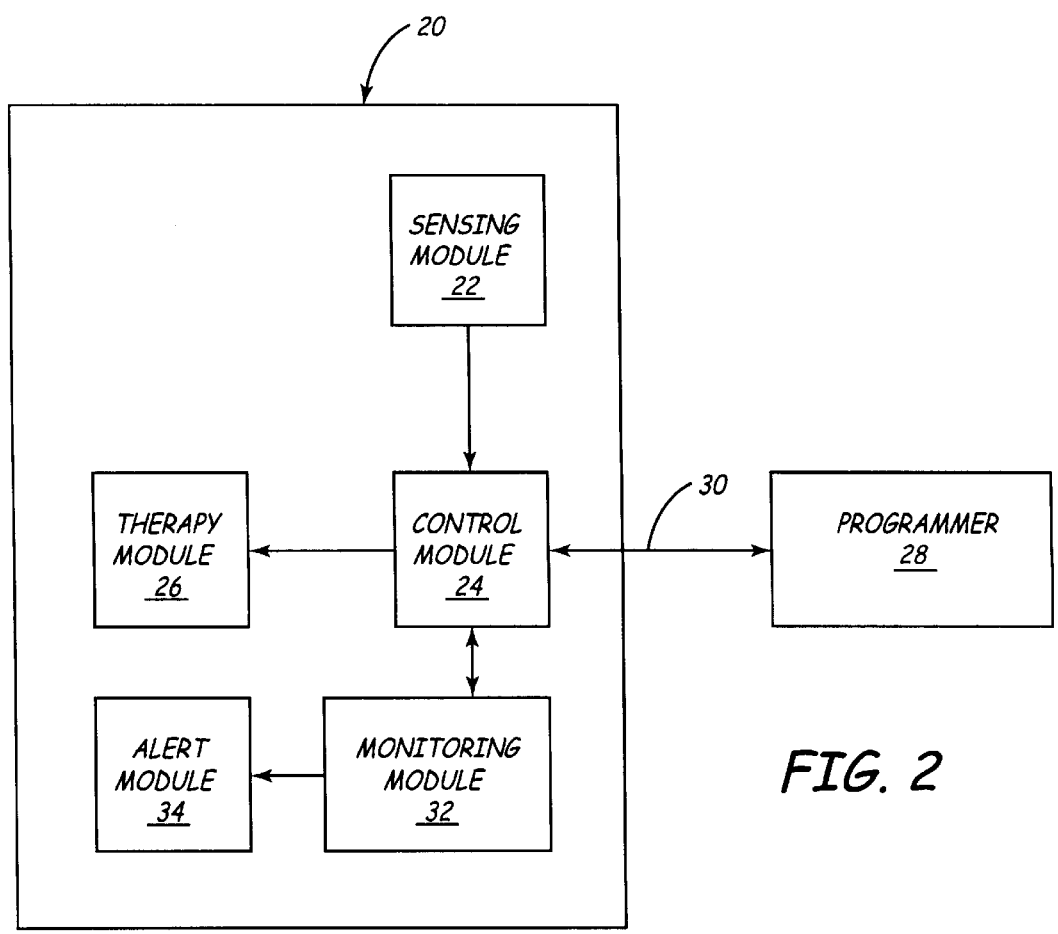
FIG. 2 is a block diagram illustrating an example implantable medical device according to an embodiment of the present invention.

FIG. 2 is a block diagram illustrating an example embodiment of an implantable medical device (IMD) 20. IMD 20 may be implemented as a variety of medical devices, such as ICD 14 of FIG. 1 or a PCD. IMD 20 includes a sensing module 22 that receives electrical signals from, for example, the heart. A control module 24 uses these signals to identify episodes during which therapy is indicated. For instance, if IMD 20 is implemented as an ICD, control module 24 analyzes cardiac electrical signals and identifies ventricular fibrillations and other arrhythmias. When therapy is indicated, control module 24 directs a therapy module 26 to administer therapy to the patient. The therapy may take any of a variety of forms, including but not limited to an electric shock or a dose of a drug.

Control module 24 may be communicatively coupled to an external programmer 28, for example, via wireless communication link 30. Using communication link 30, programmer 28 can transmit control signals to control module 24 to modify various aspects of the operation of IMD 20. Specifically, programmer 28 can enable or disable operational modes of IMD 20, including detection of and therapy for particular conditions. As a particular example, programmer 28 can place IMD 20 in one programmed state in which ventricular fibrillation (VF) detection and therapy are disabled. In another programmed state, atrial fibrillation (AF) detection and therapy may be disabled. Still other programmed states may involve disabling detection and therapy for other types of arrhythmias, such as tachycardia or bradycardia. Another programmed state may enable an operational mode in which IMD 20 induces an arrhythmia for diagnostic purposes. Any of these operational modes may harm the patient if inadvertently allowed to remain for an excessive duration, i.e., if an operator forgets to return IMD 20 to a normal operational mode.

Accordingly, IMD 20 also includes a monitoring module 32 that monitors some aspects of the operation of IMD 20. Monitoring module 32 may be implemented, for example, as a set of instructions executed by a processor and stored in a read-only memory (ROM) device in IMD 20 to monitor programmer actions that affect detection and therapy operations of IMD 20. In particular, the processor may execute the mode of operation described below in connection with FIG. 4. When monitoring module 32 detects entry of IMD 20 into a potentially harmful programmed state, it begins to time the duration of that state. At a subsequent time after control module 24 initially enters the programmed state, monitoring module 32 determines whether control module 24 is still in the same programmed state. Monitoring module 32 may perform this check at a prescribed time of day, e.g., midnight, after control module 24 enters the programmed state. Alternatively, monitoring module 32 may perform the check after a programmable number of hours, e.g., 1–24 hours, after entry into the programmed state.

If control module 24 is still in the same programmed state when monitoring module 32 performs the check, an alert module 34 issues a notification to the patient or another person. This notification may include an audible warning, a vibration, a mild electrical stimulus, or some combination of these warnings. In addition, the notification may include transmission of a radio signal to an external device, such as a transceiver that responds by contacting a physician by telephone, paging, or electronic mail. Additionally, control module 24 may automatically reactivate life-critical features, such as VF detection and therapy without human intervention.

Figure 3:
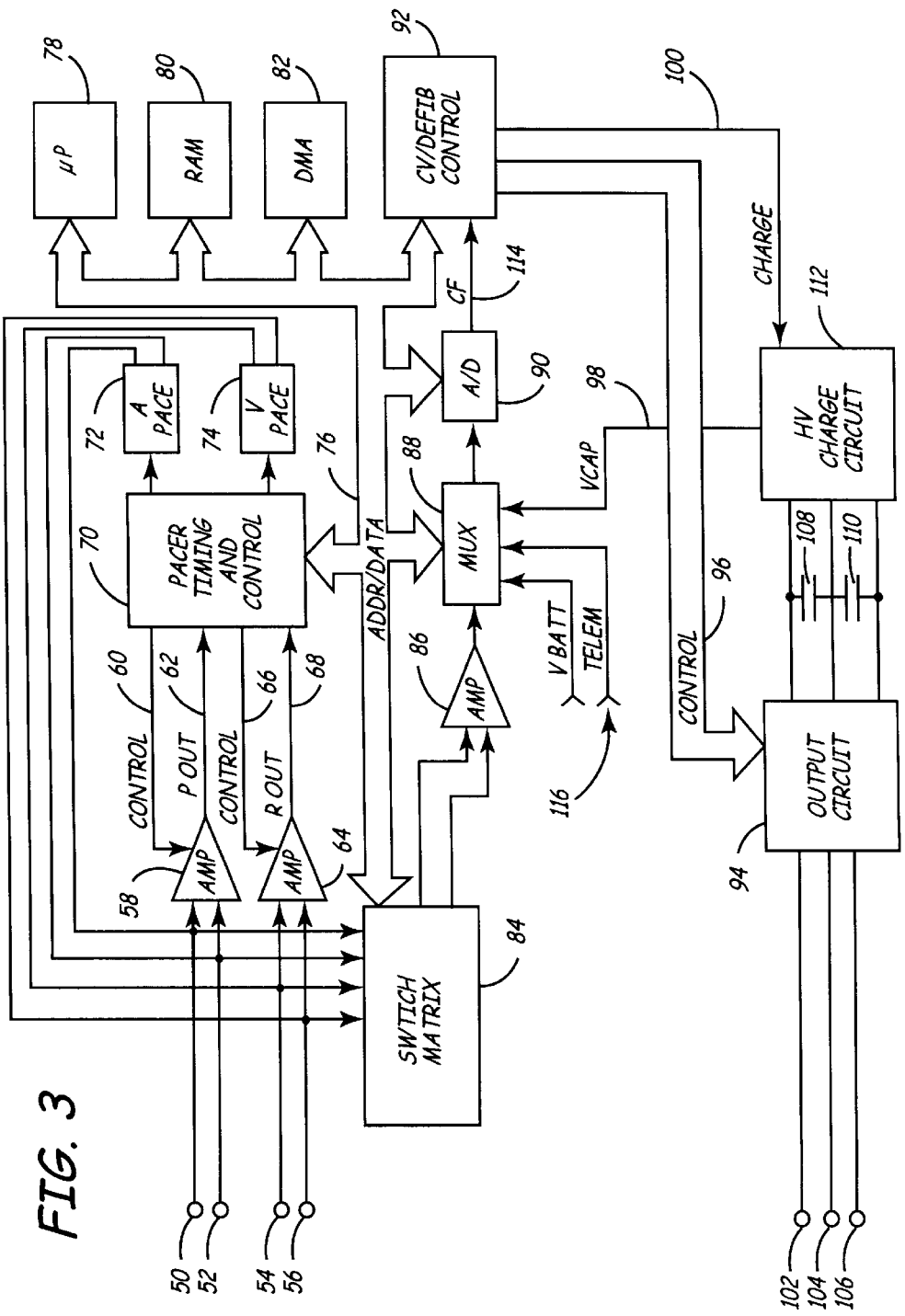
FIG. 3 is a functional schematic diagram of a medical device in which the present invention may be practiced.

FIG. 3 is a functional schematic diagram of an implantable PCD in which the present invention may be practiced. FIG. 3 should be construed as an illustrative example of one type of device in which the invention may be embodied. The invention is not limited to the particular type of device shown in FIG. 3, but may be practiced in a wide variety of device implementations, such as a pacemaker or an ICD. In addition, the invention is not limited to the implementation shown in FIG. 3. For example, the invention may be practiced in a system that includes more or fewer features than are depicted in FIG. 3.

The device illustrated in FIG. 3 is provided with an electrode system including electrodes incorporated, e.g., in leads 16 and 18 of FIG. 1. For clarity of analysis, the pacing/sensing electrodes 50, 52, 54, and 56 are shown as logically separate from pacing/defibrillation electrodes 102, 104, and 106. Some of the electrodes may be formed on the housing associated with the ICD, rather than in leads that extend from the housing.

Electrodes 102, 104, and 106 may correspond respectively to an atrial defibrillation electrode, a ventricular defibrillation electrode, and the uninsulated portion of the housing of the implantable PCD. Electrodes 102, 104, and 106 are coupled to a high voltage output circuit 94. High voltage output circuit 94 includes high voltage switches controlled by cardioversion/defibrillation (CV/defib) control logic 92 via a control bus 96. The switches within output circuit 94 control which electrodes are employed and which are coupled to the positive and negative terminals of a capacitor bank including capacitors 108 and 110 during delivery of defibrillation pulses.

Electrodes 54 and 56 may be located on or in a ventricle and are coupled to an R-wave sense amplifier 64. Operation of amplifier 64 is controlled by pacing circuitry 70 via control lines 66. Amplifier 64 may perform other functions in addition to amplification, such as filtering signals sensed by electrodes 54 and 56. Amplifier 64 may also include a comparator that compares the input signal to a pre-selected ventricular sense threshold. Amplifier 64 outputs a signal on an R-out line 68 whenever the signal sensed between electrodes 54 and 56 exceeds the ventricular sense threshold.

Electrodes 50 and 52 may be located on or in an atrium and are coupled to a P-wave sense amplifier 58. Operation of amplifier 58 is controlled by pacing circuitry 70 via control lines 60. Amplifier 58 may perform other functions in addition to amplification, such as filtering signals sensed by electrodes 50 and 52. Amplifier 58 may include a comparator that compares the input signal to a pre-selected atrial sense threshold, which is usually different from the ventricular sense threshold. Amplifier 58 outputs a signal on a P-out line 62 whenever the signal sensed between electrodes 50 and 52 exceeds the atrial sense threshold.

A switch matrix 84 selectively couples the available electrodes to a wide band (2.5–100 Hz) amplifier 86 for use in signal analysis. Signal analysis may be performed using analog circuitry, digital circuitry, or a combination of both.

A microprocessor 78 controls the selection of electrodes via a data/address bus 76. The selection of electrodes may be varied as desired. Amplifier 86 provides signals from the selected electrodes to a multiplexer 88, which provides the signals to an analog-to-digital (A/D) converter 90 for conversion to multi-bit digital signals and to a random access memory (RAM) 80 under control of a direct memory access (DMA) circuit 82 for storage.

The ICD illustrated in FIG. 3 also contains circuitry for providing cardiac pacing, cardioversion, and defibrillation therapies. For example, pacer timing/control circuitry 70 may include programmable digital counters that control the basic time intervals associated with DDD, VVI, DVI, VDD, AAI, DDI, and other modes of single and dual chamber pacing. Pacer timing/control circuitry 70 may also control escape intervals associated with anti-tachyarrhythmia pacing in both the atrium and the ventricle, employing any of a number of anti-tachyarrhythmia pacing therapies.

Intervals defined by pacing circuitry 70 include, but are not limited to, atrial and ventricular pacing escape intervals, refractory periods during which sensed P-waves and R-waves are ineffective to restart timing of the escape intervals, and pulse widths of the pacing pulses. Microprocessor 78 determines the durations of these intervals based on stored data in RAM 80 and communicates these durations to pacing circuitry 70 via address/data bus 76. Microprocessor 78 also determines the amplitude of pacing pulses and communicates this information to pacing circuitry 70.

During pacing, pacing timing/control circuitry 70 resets its escape interval counters upon sensing P-waves and R-waves as indicated by signals on lines 62 and 68. The escape interval counters are reset in accordance with the selected mode of pacing on time-out trigger generation of pacing pulses by pacer output circuits. These pacer output circuits include an atrial pacer output circuit 72 coupled to electrodes 50 and 52 and a ventricular pacer output circuit 74 coupled to electrodes 54 and 56.

Pacing timing/control circuitry 70 also resets the escape interval counters when the pacer output circuits generate pacing pulses, thereby controlling the basic timing of cardiac pacing functions, including anti-tachyarrhythmia pacing. Microprocessor 78 determines the durations of the intervals defined by the escape interval timers and communicates these durations using data/address bus 76. The value of the count present in the escape interval counters when reset by sensed R-waves and P-waves may be used to measure the durations of R-R intervals, P-P intervals, P-R intervals, and R-P intervals. These measurements are stored in RAM 80 and used to detect tachyarrhythmias.

Microprocessor 78 typically operates as an interrupt-driven device under control of a program stored in an associated read only memory (ROM, not shown) and is responsive to interrupts from pacer timing/control circuitry 70 corresponding to the occurrence of sensed P-waves and R-waves and to the generation of cardiac pacing pulses. Data/address bus 76 provides these interrupts. In response to these interrupts, microprocessor 78 performs any necessary mathematical calculations, and pacer timing/control circuitry 70 may update the values or intervals that it controls.

When an anti-tachyarrhythmia pacing regimen is indicated based on a detected atrial or ventricular tachyarrhythmia, appropriate timing intervals are loaded from microprocessor 78 into pacer timing/control circuitry 70. In the event that generation of a cardioversion or defibrillation pulse is required, microprocessor 78 employs an escape interval counter to control timing of such cardioversion and defibrillation pulses, as well as associated refractory periods.

In response to the detection of atrial or ventricular fibrillation or tachyarrhythmia requiring a cardioversion pulse, microprocessor 78 activates cardioversion/defibrillation control circuitry 92, which uses high voltage charging control lines 100 to cause a charging circuit 112 to initiate charging of high voltage capacitors 108 and 110. A VCAP line 98 monitors the voltage on high voltage capacitors 108 and 110 and communicates this information through multiplexer 88. When this voltage reaches a predetermined value set by microprocessor 78, A/D converter 90 generates a control signal on Cap Full (CF) line 114 to terminate charging. Thereafter, pacer timing/control circuitry 70 controls timing of the delivery of the defibrillation or cardioversion pulse. Following delivery of the fibrillation or tachyarrhythmia therapy, microprocessor 78 returns the device to cardiac pacing and waits for a subsequent interrupt due to pacing or the occurrence of a sensed atrial or ventricular depolarization.

An output circuit 94 delivers the cardioversion or defibrillation pulses as directed by control circuitry 92 via control bus 96. Output circuit 94 determines whether a monophasic or biphasic pulse is delivered, the polarity of the electrodes, and which electrodes are involved in delivery of the pulse. Output circuit 94 may include high voltage switches that control whether electrodes are coupled together during delivery of the pulse. Alternatively, electrodes intended to be coupled together during the pulse may simply be permanently coupled to one another, either inside or outside the device housing. Similarly, polarity may be preset in some implantable defibrillators.

Microprocessor 78 controls several aspects of the operation of the implantable IMD of FIG. 3, and may be programmed by an external programmer, such as programmer 28 of FIG. 2, to a variety of programmed states. These states may be stored, for example, as a control register in RAM 80 and may enable or disable various features of the IMD. As discussed above in connection with FIGS. 1 and 2, some programmed states may cause the IMD to enter operational modes that are potentially harmful or lethal to the patient if the IMD is not restored to its normal operational state. For example, in one such operational mode, the IMD does not detect or administer therapy for ventricular fibrillation (VF).

Figure 4:
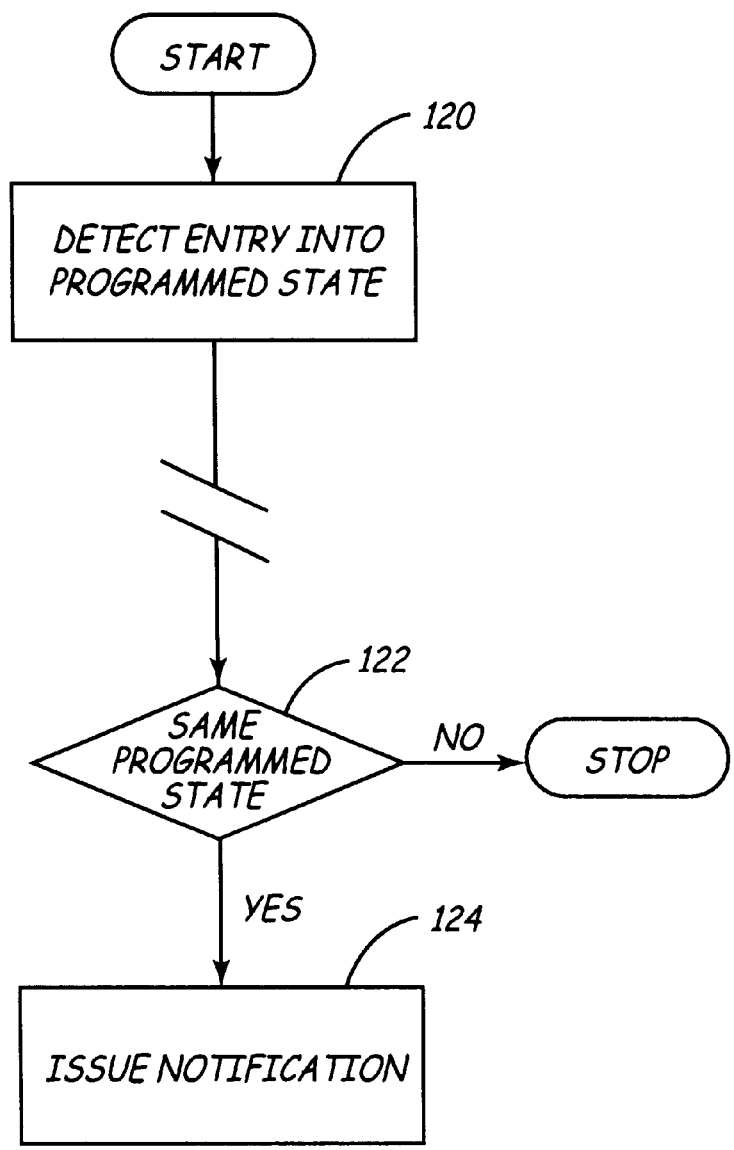
FIG. 4 is a flow diagram depicting an example mode of operation of the medical device of FIG. 3, according to another embodiment of the invention.

According to an embodiment of the invention, microprocessor 78 may avoid being inadvertently left programmed in a potentially harmful state by warning a patient or another person when it has been in such a state for a prolonged duration. One mode of operation for issuing a warning or notification is depicted in FIG. 4. This mode of operation may be controlled by a set of instructions executable by microprocessor 78. These instructions may be encoded and stored in a processor-readable medium, including, but not limited to, RAM 80 of FIG. 3, ROM, EEPROM, or flash memory.

As shown in FIG. 4, microprocessor 78 detects that it has entered a potentially harmful programmed state, such as suppression of VF detection or therapy (120). Microprocessor 78 may make this determination, for example, by periodically monitoring a control register or by receiving an interrupt indicating that the programmed state has been entered. For instance, the programmer may modify the operation of the IMD of FIG. 3 by changing a bit in the control register, thereby enabling or disabling a detection or therapy option in the IMD. Microprocessor 78 might periodically examine the control register to determine which bits, if any, have been altered, and whether any such bits correspond to potentially harmful operational states.

At a subsequent time after initially detecting entry into the programmed state, microprocessor 78 determines whether it is still in the same state, e.g., whether VF detection or therapy is still disabled (122). For example, microprocessor 78 might re-examine the control register to determine whether the bit that was altered is still in the altered state. The broken arrow in FIG. 4 indicates that this determination is made some time after microprocessor 78 was placed in the programmed state, e.g., several hours later. The time at which microprocessor 78 makes this determination may be defined as a programmable number of hours, such as 1–24 hours, after microprocessor 78 first entered the programmed state. Alternatively, microprocessor 78 may make this determination at a prescribed time of day, such as midnight, after entering the programmed state.

If microprocessor 78 is still in the potentially harmful programmed state, it causes a notification to be issued (124). This notification may include an audible alert, a vibration alert, an electrical stimulus, or a combination of these alerts. In addition, a radio signal may be sent to an external device, such as a transceiver that in turn sends a message to a pager carried by a physician. This notification warns the patient or physician that corrective action may need to be taken. The patient may respond by visiting a health care provider to have the medical device programmed to its normal mode of operation. The medical device may also be programmed to its normal mode of operation remotely. Alternatively, microprocessor 78 may automatically reset itself to normal operation without human intervention.

In some cases, a health care provider may intentionally leave the medical device in a potentially harmful state. The most common situation involves a physician-issued do-not-resuscitate order. Pursuant to such an order, for example, detection and therapy features of the medical device may be permanently disabled so that when a VF occurs, no therapy is delivered. To allow for these and other special cases, in some embodiments of the invention, the notification mode of operation of FIG. 4 may be disabled by setting or resetting a bit in a control register, such that warnings are not issued. Notification may also be suppressed, for example, until the time of implantation to avoid inappropriate warnings during shipping prior to implantation.

Accordingly, various embodiments of the invention may reduce the likelihood that an implantable medical device will be left in a potentially harmful operational state for an extended duration. By alerting a patient when the implantable medical device has been left in a potentially harmful programmed state for an extended duration, the invention may mitigate the risk of harm to the patient due to human error. For example, if ventricular fibrillation (VF) detection or therapy is programmed to a disabled state and inadvertently left in that state, i.e., is not enabled again in a timely manner, issuing an alert to the patient may prompt the patient to make an office visit to have VF detection and therapy reactivated. As a result, VF and other therapies are more likely to be delivered when needed. Various embodi-

What is claimed is:

1. A method for indicating a programmed state of an implantable medical device, the method comprising:
    detecting a programmed state of the implantable medical device;
    subsequently determining whether the implantable medical device is in the programmed state similar to the detected programmed state; and
    issuing a notification when the implantable medical device is in the same programmed state.

2. The method of claim 1, wherein the programmed state comprises a disabled state of at least one of ventricular fibrillation detection and ventricular fibrillation therapy.

3. The method of claim 1, wherein the programmed state comprises a disabled state of at least one of atrial fibrillation detection and atrial fibrillation therapy.

4. The method of claim 1, wherein the programmed state comprises a disabled state of at least one of atrial tachycardia detection, ventricular tachycardia detection, atrial tachycardia therapy, and ventricular tachycardia therapy.

5. The method of claim 1, wherein the programmed state comprises a disabled state of at least one of bradycardia detection and bradycardia therapy.

6. The method of claim 1, wherein the programmed state comprises an enabled state of induction of arrhythmia.

7. The method of claim 1, wherein the subsequent determination occurs at a set time of day following detecting the programmed state.

8. The method of claim 1, wherein the subsequent determination occurs at elapsing of a programmable duration following detecting the programmed state.

9. The method of claim 1, wherein the notification comprises at least one of a notification sent to a device external to the implantable medical device, an audible alert, a vibration alert, and an electrical stimulation alert.

10. The method of claim 1, further comprising suppressing the notification.

11. The method of claim 1, further comprising automatically exiting the programmed state.

12. A processor-readable medium containing instructions to cause a processor to:
    detect a programmed state of an implantable medical device;
    at a subsequent time after detecting the programmed state, determine whether the implantable medical device is in the same programmed state; and
    when the implantable medical device is in the same programmed state, issue a notification.

13. The processor-readable medium of claim 12, wherein the programmed state comprises a disabled state of at least one of ventricular fibrillation detection and ventricular fibrillation therapy.

14. The processor-readable medium of claim 12, wherein the programmed state comprises a disabled state of at least one of atrial fibrillation detection and atrial fibrillation therapy.

15. The processor-readable medium of claim 12, wherein the programmed state comprises a disabled state of at least one of atrial tachycardia detection, ventricular tachycardia detection, atrial tachycardia therapy, and ventricular tachycardia therapy.

16. The processor-readable medium of claim 12, wherein the programmed state comprises a disabled state of at least one of bradycardia detection and bradycardia therapy.

17. The processor-readable medium of claim 12, wherein the programmed state comprises an enabled state of induction of arrhythmia.

18. The processor-readable medium of claim 12, wherein the subsequent time occurs at a set time of day following detecting the programmed state.

19. The processor-readable medium of claim 12, wherein the subsequent time occurs at elapsing of a programmable duration following detecting the programmed state.

20. The processor-readable medium of claim 12, wherein the notification comprises at least one of a notification sent to a device external to the implantable medical device, an audible alert, a vibration alert, and an electrical stimulation alert.

21. The processor-readable medium of claim 12, containing further processor-executable instructions to cause the processor to suppress the notification.

22. The processor-readable medium of claim 12, containing further processor-executable instructions to cause the processor to automatically exit the programmed state.

23. An implantable medical device comprising:
    a control module programmable to a programmed state;
    a monitoring module to detect the programmed state; and
    an alert module to issue a notification when the control module remains in the programmed state at a subsequent time after the monitoring module detects the programmed state.

24. The implantable medical device of claim 23, wherein the programmed state comprises a disabled state of at least one of ventricular fibrillation detection and ventricular fibrillation therapy.

25. The implantable medical device of claim 23, wherein the programmed state comprises a disabled state of at least one of atrial fibrillation detection and atrial fibrillation therapy.

26. The implantable medical device of claim 23, wherein the programmed state comprises a disabled state of at least one of atrial tachycardia detection, ventricular tachycardia detection, atrial tachycardia therapy, and ventricular tachycardia therapy.

27. The implantable medical device of claim 23, wherein the programmed state comprises a disabled state of at least one of bradycardia detection and bradycardia therapy.

28. The implantable medical device of claim 23, wherein the programmed state comprises an enabled state of induction of arrhythmia.

29. The implantable medical device of claim 23, wherein the subsequent time occurs at a set time of day following detecting the programmed state.

30. The implantable medical device of claim 23, wherein the subsequent time occurs at elapsing of a programmable duration following detecting the programmed state.

31. The implantable medical device of claim 23, wherein the notification comprises at least one of a notification sent to a device external to the implantable medical device, an audible alert, a vibration alert, and an electrical stimulation alert.

32. The implantable medical device of claim 23, wherein the alert module is programmable to suppress the notification.

33. The implantable medical device of claim 23, wherein the control module is programmable to automatically exit the programmed state.

* * * * *